(12) United States Patent
Dwari et al.

(10) Patent No.: US 12,222,449 B2
(45) Date of Patent: Feb. 11, 2025

(54) VIBRATION BASED ACTUATOR SYSTEM FOR CLEANING OF OPTICAL SURFACE

(71) Applicant: Carrier Corporation, Palm Beach Gardens, FL (US)

(72) Inventors: Suman Dwari, Vernon, CT (US); Rajiv Ranjan, South Windsor, CT (US); Peter R. Harris, West Hartford, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 1059 days.

(21) Appl. No.: 17/054,431

(22) PCT Filed: May 6, 2019

(86) PCT No.: PCT/US2019/030905
§ 371 (c)(1),
(2) Date: Nov. 10, 2020

(87) PCT Pub. No.: WO2019/221957
PCT Pub. Date: Nov. 21, 2019

(65) Prior Publication Data
US 2021/0080552 A1    Mar. 18, 2021

Related U.S. Application Data

(60) Provisional application No. 62/671,855, filed on May 15, 2018.

(51) Int. Cl.
*G01S 7/481* (2006.01)
*G01N 21/53* (2006.01)
(Continued)

(52) U.S. Cl.
CPC ............ *G01S 7/4817* (2013.01); *G01N 21/53* (2013.01); *G01N 33/0036* (2013.01);
(Continued)

(58) Field of Classification Search
CPC .... G01S 7/4813; G01S 7/4814; G01S 7/4817; G01S 7/497; G01S 2007/4977;
(Continued)

(56) References Cited

U.S. PATENT DOCUMENTS

| 4,929,072 A | 5/1990 | Fujie et al. |
| 6,226,933 B1 | 5/2001 | Nelson et al. |

(Continued)

FOREIGN PATENT DOCUMENTS

| JP | 2981600 B2 * | 11/1999 |
| RU | 106784 U1 | 7/2011 |

(Continued)

OTHER PUBLICATIONS

J. Martins, M. Kersch, V. Altstädt, R. Oliveira, Electrical conductivity of poly(vinylidene fluoride)/polyaniline blends under oscillatory and steady shear conditions, 2013, Polymer Testing, 32 (2013), pp. 1 and 2. (Year: 2013).*

(Continued)

*Primary Examiner* — Yuqing Xiao
*Assistant Examiner* — Benjamin Richard Hebert
(74) *Attorney, Agent, or Firm* — CANTOR COLBURN LLP (57) ABSTRACT

A scanner of an optical detection system includes a housing, an optical surface coupled to the housing, and an actuator coupled to the optical surface. The optical surface is movable to direct light into an area being scanned and to receive a reflected light pulse from the area being scanned. The actuator is operable to agitate the optical surface to remove debris from the optical surface.

19 Claims, 11 Drawing Sheets

(51) Int. Cl.
   *G01N 33/00* (2006.01)
   *G01S 7/497* (2006.01)
   *G01S 17/89* (2020.01)
   *G02B 27/00* (2006.01)
   *G08B 17/107* (2006.01)
   *H02N 2/10* (2006.01)
   *H10N 30/857* (2023.01)

(52) U.S. Cl.
   CPC .......... *G01S 17/89* (2013.01); *G02B 27/0006* (2013.01); *G08B 17/107* (2013.01); *G01S 2007/4977* (2013.01); *H02N 2/103* (2013.01); *H10N 30/857* (2023.02)

(58) Field of Classification Search
   CPC .... G01S 17/89; G01N 21/53; G01N 33/0036; G02B 26/0816; G02B 27/0006; G08B 17/107; H02N 2/103; H10N 30/857
   See application file for complete search history.

(56) References Cited

U.S. PATENT DOCUMENTS

| | | | |
|---|---|---|---|
| 6,338,560 B1* | 1/2002 | Abedian | G02B 27/0006 359/508 |
| 6,452,672 B1 | 9/2002 | Trainoff | |
| 6,543,110 B1 | 4/2003 | Pelrine et al. | |
| 6,956,348 B2 | 10/2005 | Landry et al. | |
| 7,324,148 B2 | 1/2008 | Takizawa et al. | |
| 7,786,392 B2 | 8/2010 | Hickman | |
| 7,878,056 B2 | 2/2011 | Huang et al. | |
| 8,253,578 B2 | 8/2012 | Watabe et al. | |
| 8,842,204 B2 | 9/2014 | Lin | |
| 8,980,010 B2 | 3/2015 | Ifuku et al. | |
| 9,810,991 B2 | 11/2017 | Chilese et al. | |
| 9,897,802 B2 | 2/2018 | Inukai | |
| 2005/0225743 A1* | 10/2005 | Chang | G01S 7/481 356/5.01 |
| 2008/0236613 A1 | 10/2008 | Hsiao | |
| 2009/0109512 A1* | 4/2009 | Park | G02B 26/0833 359/198.1 |
| 2012/0062867 A1* | 3/2012 | Shibatani | G01C 3/085 356/4.01 |
| 2015/0334277 A1* | 11/2015 | Liu | G02B 27/0006 348/374 |
| 2017/0160542 A1* | 6/2017 | Mouri | G02B 27/0006 |
| 2018/0284244 A1* | 10/2018 | Russell | G01S 7/4868 |
| 2018/0329206 A1* | 11/2018 | Cohen | B08B 7/028 |
| 2019/0324262 A1* | 10/2019 | Miller | B81B 3/0083 |

FOREIGN PATENT DOCUMENTS

| | | |
|---|---|---|
| WO | 2009134145 A1 | 11/2009 |
| WO | 2017149526 A2 | 9/2017 |

OTHER PUBLICATIONS

European Office Action; European Application No. 19729391.3; Date: Aug. 10, 2022; 5 pages.

Caldwell, Tom. "Sensor Kitted with Dust Removal Vibration", Ricoh Talk Forum: Digital Photography Review; pp. 1-5; Sep. 11, 2017; Date Accessed: Nov. 10, 2020.

International Search Report of the International Searching Authority; International Application No. PCT/US2019/030905; International Filing Date: May 6, 2019; Date of Mailing: Jul. 30, 2019; 4 pages.

Ricardo Pres et al.: "Study of Polyvinylidene Fluoride (PVDF) Based Bimorth Actuators for Laser Scanning Actuation at kHz Frequency Range", Sensors and Actuators A: Physical, Elsevier BV, NL, vol. 183, May 10, 2012 (May 10, 2012), pp. 84-94, XP028428459, ISSN: 0924-4247, DOI: 10.1016/J.SNA.2012.05.019 [retrieved on Jun. 2, 2012].

Written Opinion of the International Searching Authority; International Application No. PCT/US2019/030905; International Filing Date: May 6, 2019; Date of Mailing: Jul. 30, 2019; 6 pages.

* cited by examiner

FIG. 11

VIBRATION BASED ACTUATOR SYSTEM FOR CLEANING OF OPTICAL SURFACE

CROSS REFERENCE TO RELATED APPLICATIONS

This application is a National Stage application of PCT/US2019/030905 filed May 6, 2019, which claims priority to U.S. Provisional application 62/671,855 filed May 15, 2018, both of which are incorporated by reference in their entirety herein.

BACKGROUND

Embodiments of the disclosure relate generally to a detection system associated with a predetermined space and, more particularly, to an actuator for use with a beam based optical detection systems.

Light detection and ranging, and other beam based optical detection systems may be used to detect the presence of smoke and other particulates within a space. These systems include one or more sensors or non-contact measurement devices that work by emitting a very narrow light pulse and analyzing the reflection of the light pulse from an object. To evaluate a two or three dimensional area from a single observation position, these sensors typically includes either multiple beams or a movable optical surface.

Actuators are commonly used to rotate the optical surface to reflect the emitted light through an area. However, such actuation systems have several disadvantages. For example, the motor and corresponding mechanical system increases the size and weight of each sensor. In addition, due to the mechanical nature of the actuation system, the overall reliability of the system is limited, and the costs associated with maintenance are high. In addition, existing actuation systems typically consume substantial amounts of power and have existing operating limitations over the range of actuation.

Over time, debris and dust accumulate on the optical surfaces of non-contact measurement devices, thereby reducing their operational accuracy. Maintenance is typically performed by manually cleaning these surfaces. Accordingly, standard maintenance procedures are not only expensive but time consuming.

BRIEF DESCRIPTION

According to an embodiment, a scanner of an optical detection system includes a housing, an optical surface coupled to the housing, and an actuator coupled to the optical surface. The optical surface is movable to direct light into an area being scanned and to receive a reflected light pulse from the area being scanned. The actuator is operable to agitate the optical surface to remove debris from the optical surface.

In addition to one or more of the features described above, or as an alternative, in further embodiments comprising: a light source associated with the housing operable to emit a light pulse into the area being scanned and a light sensitive device associated with the housing operable to detect the reflected light pulse from the area being scanned.

In addition to one or more of the features described above, or as an alternative, in further embodiments the actuator agitates the optical surface at a frequency between about 1 Hz and 1 kHz.

In addition to one or more of the features described above, or as an alternative, in further embodiments the actuator is selectively operable to rotate the optical surface about at least one axis relative to the housing.

In addition to one or more of the features described above, or as an alternative, in further embodiments the actuator comprises a solid state flexible polymer deformable in response to application of a voltage to the solid state flexible polymer.

In addition to one or more of the features described above, or as an alternative, in further embodiments the actuator is directly coupled to the optical surface.

In addition to one or more of the features described above, or as an alternative, in further embodiments the actuator is indirectly coupled to the optical surface.

In addition to one or more of the features described above, or as an alternative, in further embodiments the actuator further comprises a first electrode and a second electrode operable to apply the voltage to the solid state flexible polymer.

In addition to one or more of the features described above, or as an alternative, in further embodiments the solid state flexible polymer comprises an electroactive polymer.

In addition to one or more of the features described above, or as an alternative, in further embodiments the solid state flexible polymer comprises a piezoelectric material.

In addition to one or more of the features described above, or as an alternative, in further embodiments the solid state flexible polymer comprises a dielectric polymer.

In addition to one or more of the features described above, or as an alternative, in further embodiments the scanner further comprises another actuator operably coupled to at least one of the optical surface and the housing.

In addition to one or more of the features described above, or as an alternative, in further embodiments the another actuator is an electromechanical actuator.

In addition to one or more of the features described above, or as an alternative, in further embodiments the actuator indirectly couples the another actuator to the optical surface.

According to another embodiment, a smoke detection system includes a central processing unit and at least one scanner in communication with the central processing unit. The at least one scanner includes an optical surface associated with the housing. The optical surface is movable relative to the housing. An actuator is operably coupled to the optical surface and is operable to agitate the optical surface to remove debris from the optical surface.

In addition to one or more of the features described above, or as an alternative, in further embodiments comprising a housing and a light sensitive device operable to detect a reflected light pulse from an area being scanned. The light sensitive device is coupled to the housing and arranged in communication with the central processing unit.

In addition to one or more of the features described above, or as an alternative, in further embodiments comprising a light source associated with the housing operable to emit a light pulse into the area being scanned, wherein the actuator is operable to move at least one of the optical surface and the housing to move the light pulse through the area being scanned.

In addition to one or more of the features described above, or as an alternative, in further embodiments the actuator is a solid state flexible polymer deformable in response to application of a voltage to the solid state flexible polymer.

In addition to one or more of the features described above, or as an alternative, in further embodiments the actuator further comprises a first electrode and a second electrode operable to apply the voltage to the solid state flexible polymer.

In addition to one or more of the features described above, or as an alternative, in further embodiments comprising another actuator, separate from the actuator, the another actuator being operably coupled to at least one of the optical surface and the housing to move the light pulse through the area being scanned.

According to yet another embodiment, a method of cleaning a scanner of a detection system includes initiating a cleaning operation and moving an optical surface of the scanner at a frequency of at least 1 Hz via an actuator coupled to the optical surface to remove debris from the optical surface.

In addition to one or more of the features described above, or as an alternative, in further embodiments the frequency is between 1 Hz and 1 kHz.

In addition to one or more of the features described above, or as an alternative, in further embodiments initiating the cleaning operation occurs in response to detection of a degradation of strength of a light pulse emitted from the scanner.

In addition to one or more of the features described above, or as an alternative, in further embodiments initiating the cleaning operation occurs at designated time intervals.

In addition to one or more of the features described above, or as an alternative, in further embodiments moving the optical surface of the scanner at a frequency of at least 1 Hz via the actuator coupled to the optical surface continues for a predetermined period of time.

In addition to one or more of the features described above, or as an alternative, in further embodiments moving the optical surface of the scanner at a frequency of at least 1 Hz via the actuator coupled to the optical surface continues until a strength of a light pulse emitted from the scanner has increased beyond a threshold.

In addition to one or more of the features described above, or as an alternative, in further embodiments moving the optical surface of the scanner at a frequency of at least 1 Hz via the actuator occurs in response to a command from a controller.

In addition to one or more of the features described above, or as an alternative, in further embodiments the command from the controller comprises at least one of an angle command and a vibration command.

BRIEF DESCRIPTION OF THE DRAWINGS

The following descriptions should not be considered limiting in any way.

With reference to the accompanying drawings, like elements are numbered alike.

DETAILED DESCRIPTION

A detailed description of one or more embodiments of the disclosed apparatus and method are presented herein by way of exemplification and not limitation with reference to the Figures.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

Figure 1:
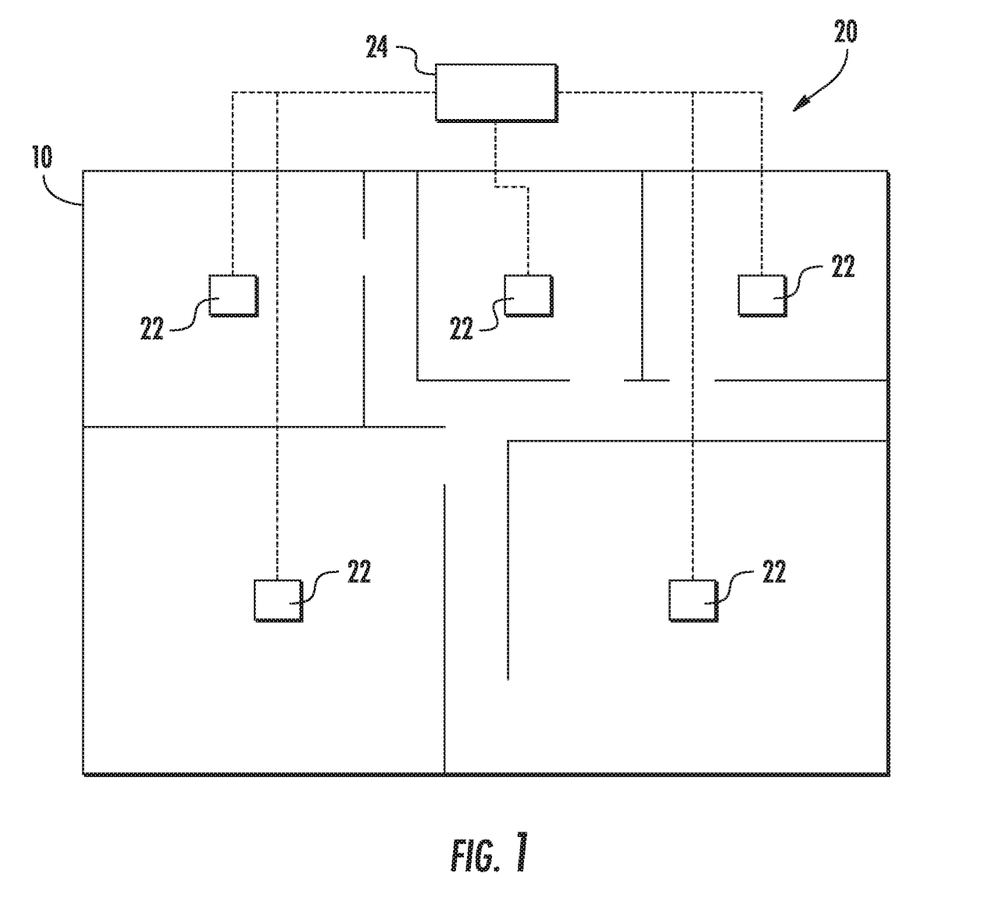
FIG. 1 is a schematic diagram of an optical detection system associated with a building.

With reference now to FIG. 1, an optical system 20 for monitoring one or more conditions, such as the presence of smoke, fire, or other contaminants within an environment 10 is illustrated. As shown, the optical system 20 includes one or more non-contact measurement devices 22 arranged at various positions, such as rooms for example, throughout the building or area 10 being monitored. By positioning the non-contact measurement devices 22 at distinct positions or locations, a larger space or area may be monitored by the optical system. In addition, inclusion of multiple non-contact measurement devices 22 at distinct positions allows for more accurate detection of an object or particle.

In the illustrated, non-limiting embodiment, each of the non-contact measurement devices 22 is operably coupled or in communication with a central processing unit or station 24. The connection between the non-contact measurement devices 22 and the central processing unit 24 may include a wired, a wireless, or optical connection, or any other suitable type of connection known in the art. However, in other embodiments, the system 20 may include a plurality of processing units 24, for example such that each non-contact measurement device 22 is associated with a corresponding processing unit 24. The plurality of processing units 24 may be separate from or integrally formed with the non-contact measurement devices 22. In an embodiment, the non-contact measurement devices 22 emit a light pulse and analyze a reflected light pulse to determine the presence of an object or particle within the space being monitored. Examples of such optical systems 20 include but are not limited to a Light detection and ranging (LIDAR) system, a fiber optic beam detection system, and as well as passive optical sensors like a passive infrared security sensor for example.

Figure 2:
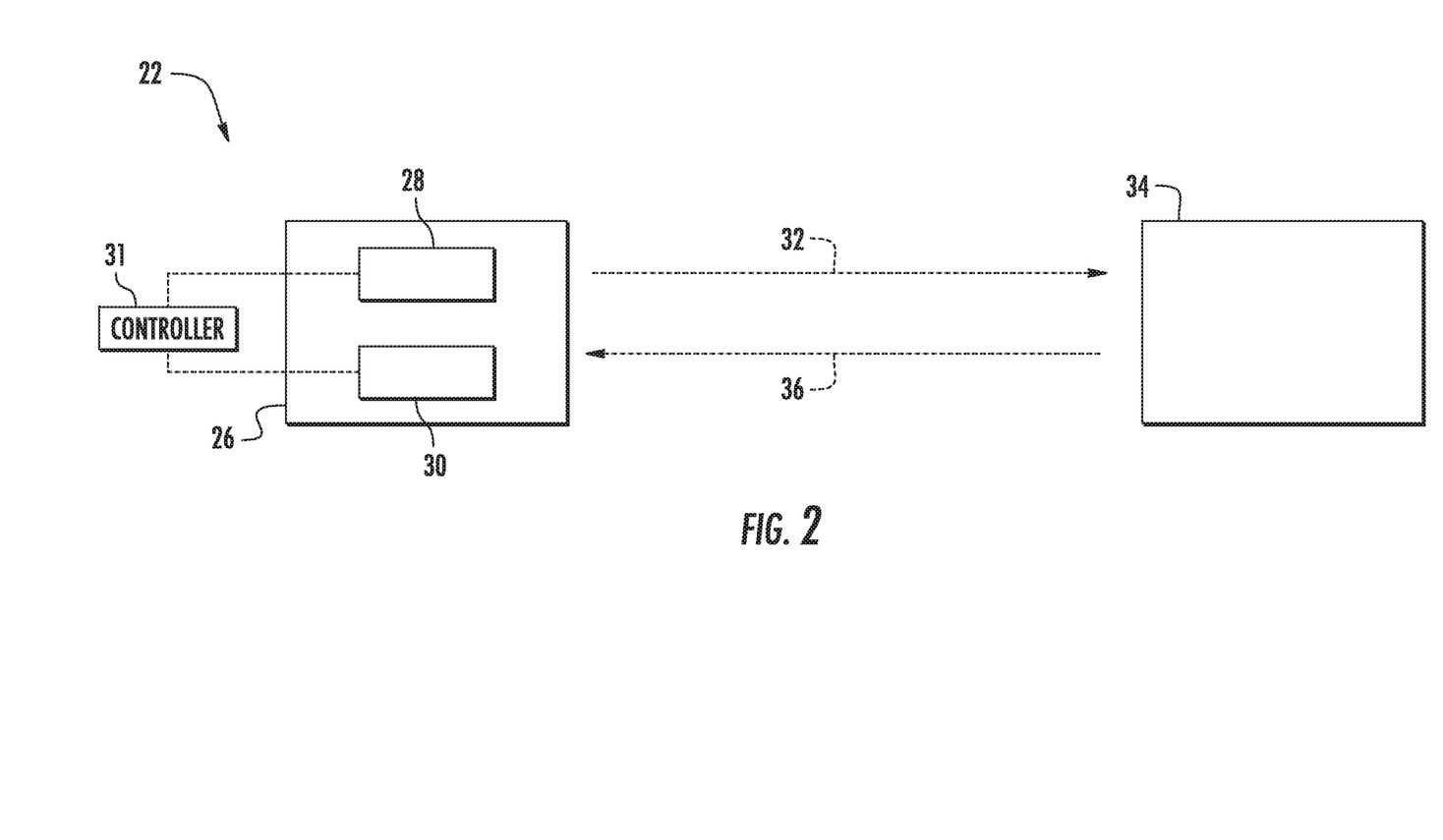
FIG. 2 is a schematic diagram of a scanner of an optical detection system.
Figure 3:
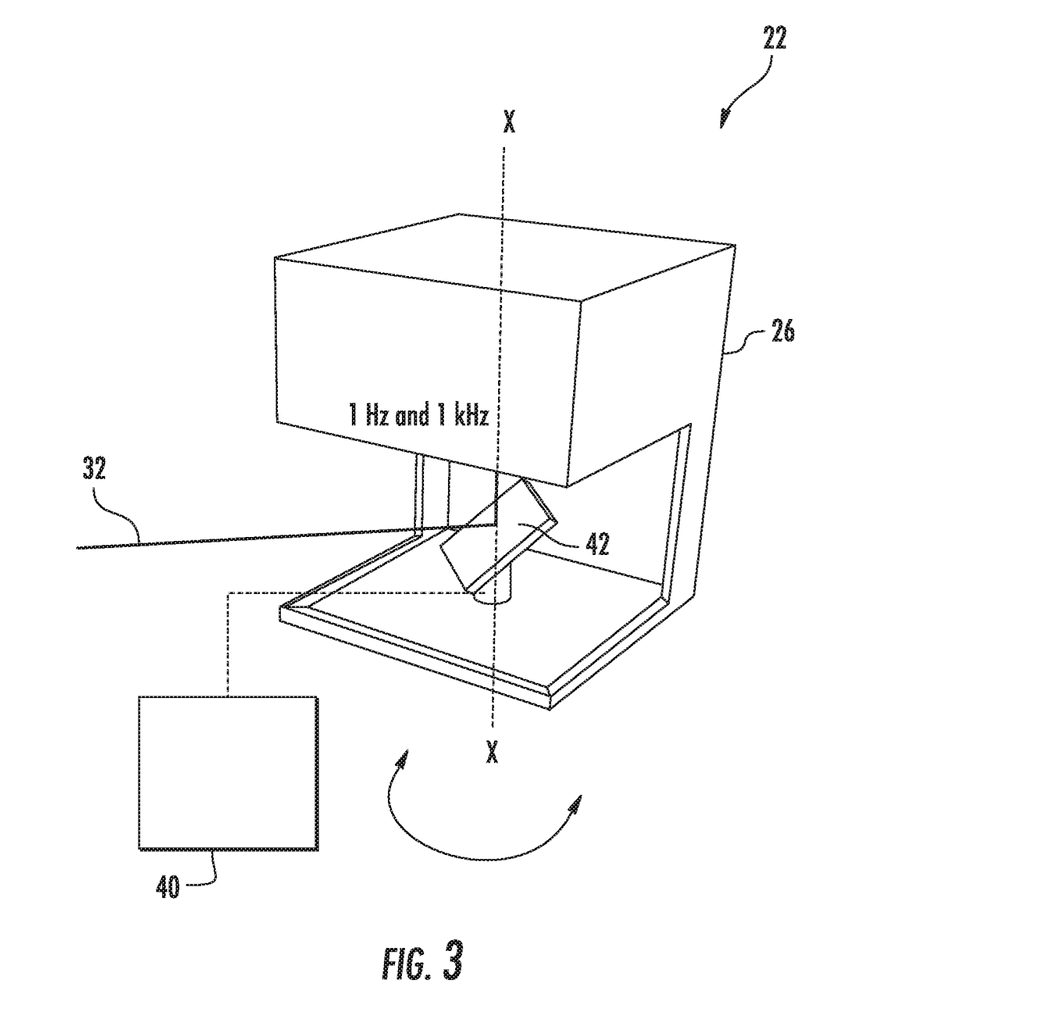
FIG. 3 is a perspective view of a scanner of an optical detection system.
Figure 4:
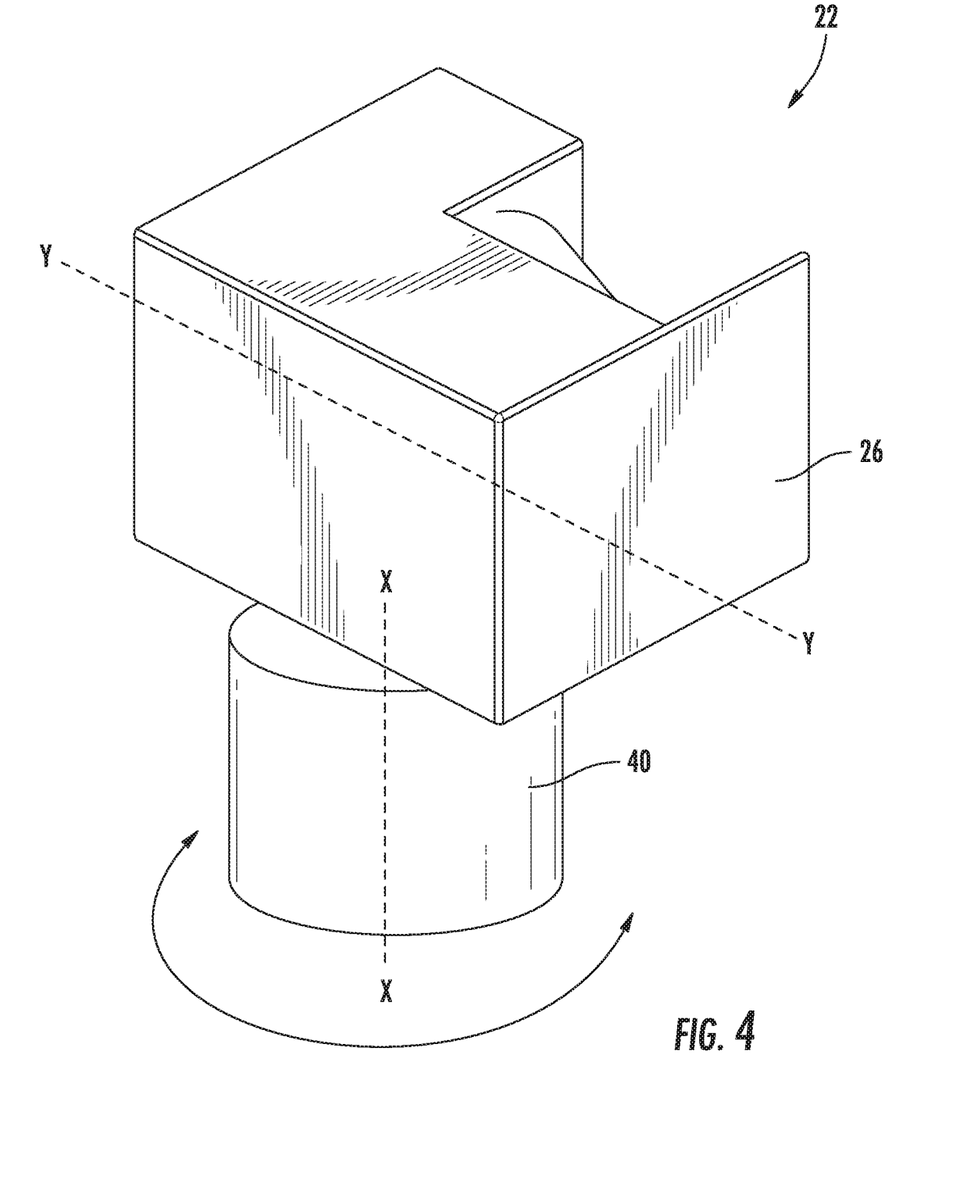
FIG. 4 is a perspective view of another scanner of an optical detection system.

With reference to FIGS. 2-4, an example of an optical non-contact measurement device 22 of such an optical system 20 is illustrated. The optical non-contact measurement device 22 is referred to herein as a scanner. The scanner 22 includes a housing 26 containing a light source 28 and a light sensitive device 30, such as laser diode used for emitting a light pulse and a photodiode for receiving a light pulse. Any light source 28 operable to emit a light having a suitable wavelength, including but not limited to, infrared, ultraviolet, or light within the visible spectrum for example, may be used. The light source 28 may be selected based on not only the environment in which the non-contact measurement device is located, but also the type of particle or contaminant being targeted by the device 22 for detection.

The light pulse, illustrated schematically at 32 in FIG. 2, emitted by the light source 28 is reflected by an object or particle 34 as a reflected pulse, illustrated schematically at 36, which is received by the detector 30. A controller 31 is operably coupled to both the light source 28 and the light sensitive device 30 to control emission of light by the scanner and analyze the reflected light received by the light sensitive device 30.

In order to scan a three dimensional (3D) area from a single location, one or more actuators 40 are operable to rotate one or more components (FIG. 3) of the scanner 22 to reflect the light pulse 32 through the area surrounding the scanner 22. In the non-limiting embodiment illustrated in FIG. 3, the one or more movable components of the scanner 22 includes an optical surface 42, such as a mirror for example, that is rotatable about an axis by the actuator 40. However, it should be understood that in other embodiments, the one or more actuators 40 may be operable to rotate the scanner 22 in its entirety, as shown in FIG. 4.

Electronics, such as wiring, a communication module, a memory, and the central processing unit 24, are used to process and calculate the precise coordinates of the scanned object or particle 34 based on the calculated travel time of the emitted and reflected pulses 32, 36 and the angles of displacement of the actuator 40 and the optical surface 42. As a result of the redirection of the light through the area, a map of precise distance measurements of the scene from the observation position of the scanner 22 may be created.

However, in other embodiments, a scanning passive infrared detector could be used in place of the scanner. In such embodiments, the detector does not include a light source, and as a result, the central processing unit 24 may be configured to evaluate an area using only the light reflected from the area.

Figure 5:
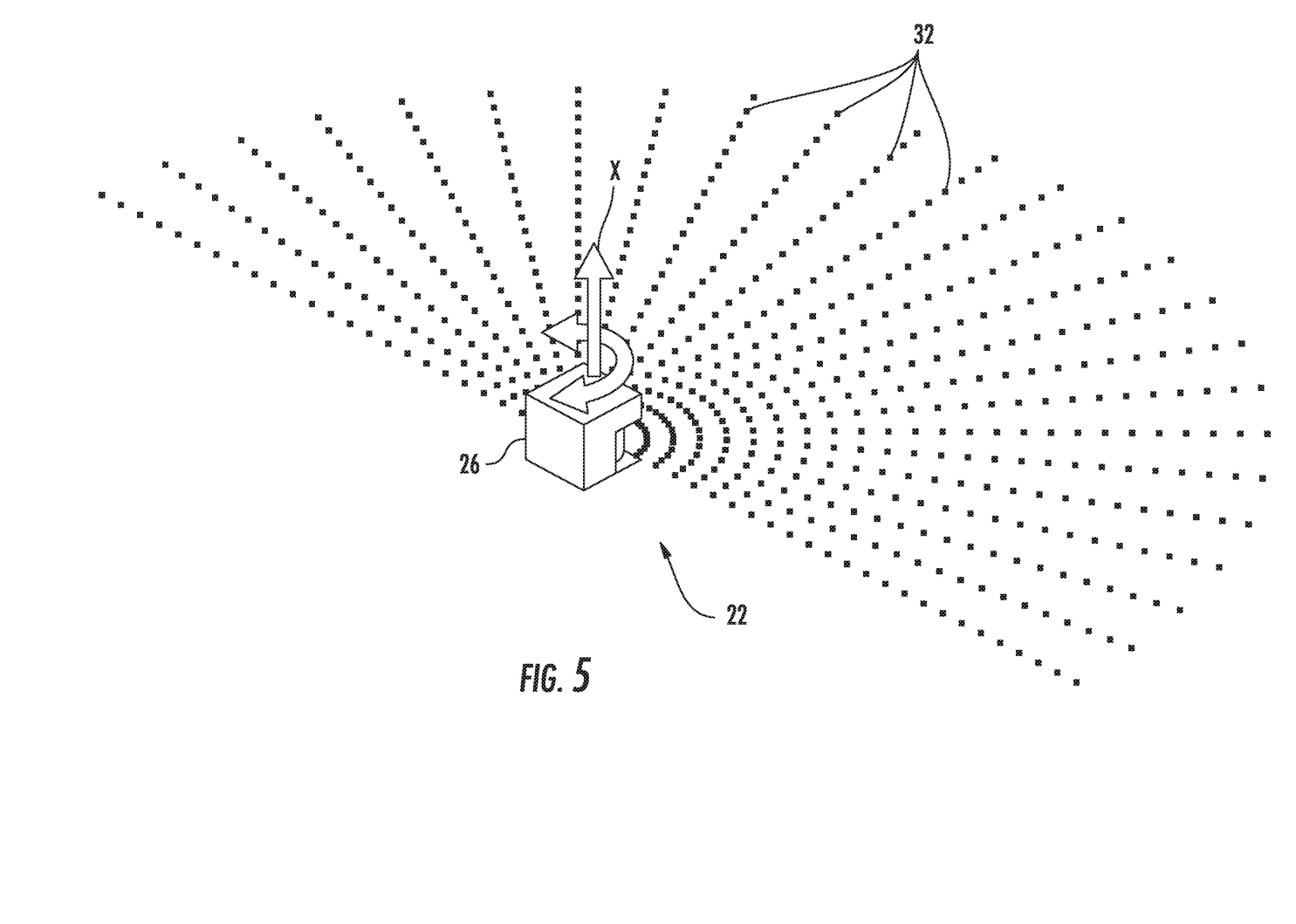
FIG. 5 is a perspective view of a light pulse emission within a region surrounding the scanner.

The optical surface 42 (or scanner 22) may be configured to rotate about at least one axis in both a first direction, and a second, opposite direction. In embodiments where the optical surface 42 (or scanner 22) is rotatable about a plurality of axes, a first axis of rotation and a second axis of rotation may be oriented substantially perpendicular to one another. In the illustrated, non-limiting embodiment of FIG. 3, the optical surface 42 is rotatable about at least a vertically oriented axis X. However, in other embodiments, the at least one axis may be a horizontally oriented axis Y, as shown in FIG. 4. Referring to FIG. 5, rotation of the optical surface 42 (or scanner 22) about the vertical axis X, results in a two dimensional distribution of emitted pulses, represented by the straight dotted lines in a horizontal plane 32. Similarly, rotation of the optical surface 42 (or scanner 22) about a horizontally oriented axis Y would result in a two dimensional distribution of emitted pulses in a vertical plane. Accordingly, rotation of the optical surface 42 (or scanner 22) about both the vertical and horizontal axes X, Y results in a distribution of emitted pulses through a three dimensional space.

In existing optical detection systems 20, the actuator(s) 40 used to move the optical surface 42 or the scanner 22 is typically an electromagnetic motor. With reference now to FIGS. 6-9, in an embodiment, the actuator 40 configured to move the optical surface 42 is a solid state flexible actuator operable by transforming electrical energy into mechanical energy. Examples of a solid state flexible actuators include, but are not limited to an electroactive polymer based actuator, a dielectric polymer actuator, an ionic polymer actuator, a piezoelectric material, or any other suitable stimuli responsive polymer.

Figure 6A:
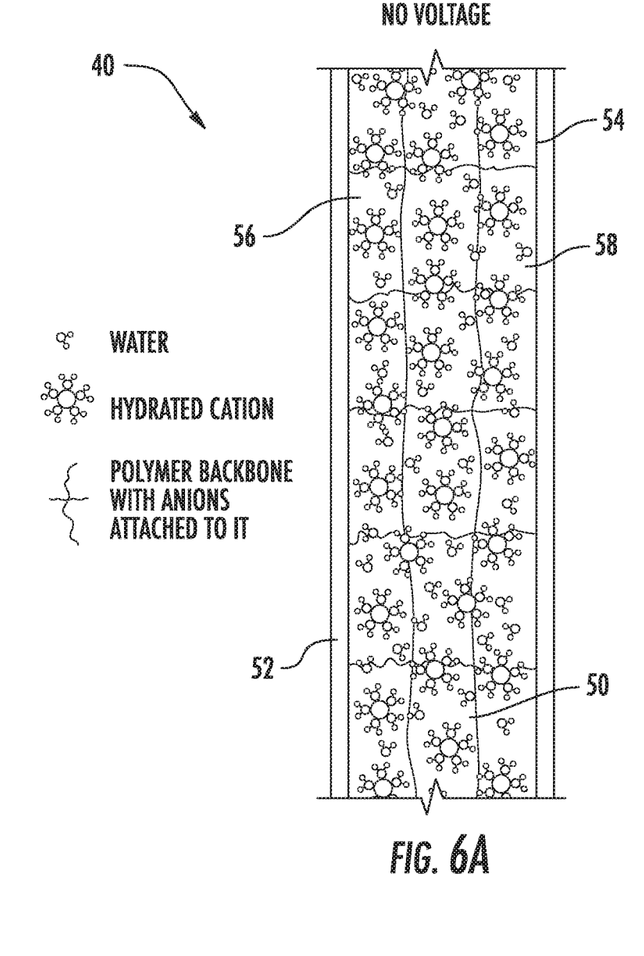
FIG. 6A is a cross-sectional view of a solid state flexible actuator in a non-actuated state according to an embodiment.

An embodiment of a solid state flexible actuator 40 is shown in FIG. 6A. As shown, the actuator 40 includes a portion of an electroactive polymer 50 that acts as an insulating dielectric between two electrodes 52, 54. In the illustrated, non-limiting embodiment, the electroactive polymer includes water and hydrated cation molecules supported by a polymer backbone having anions attached thereto. However, an electroactive polymer 50 having any suitable construction is contemplated herein. The electroactive polymer 50 may deflect upon application of a voltage difference between the two electrodes 52, 54 (a 'dielectric elastomer'). As shown, the first electrode 52 and the second electrode 54 are attached to the polymer 50 at a first surface 56 and a second surface 58, respectively, to provide a voltage difference across polymer 50, or to receive electrical energy from the polymer 50.

It should be understood that embodiments where the actuator 40 includes more than two electrodes are also contemplated herein. For example, in FIG. 8 multiple electrodes are fabricated at various angular locations about the electroactive polymer rod 50. Accordingly, the voltage may be controlled between any pair of the plurality of electrodes to facilitate movement of the polymer 50 in a plurality of directions. As shown, inclusion of multiple electrodes provides enhanced control of the movement of the polymer rod 50.

Figure 6B:
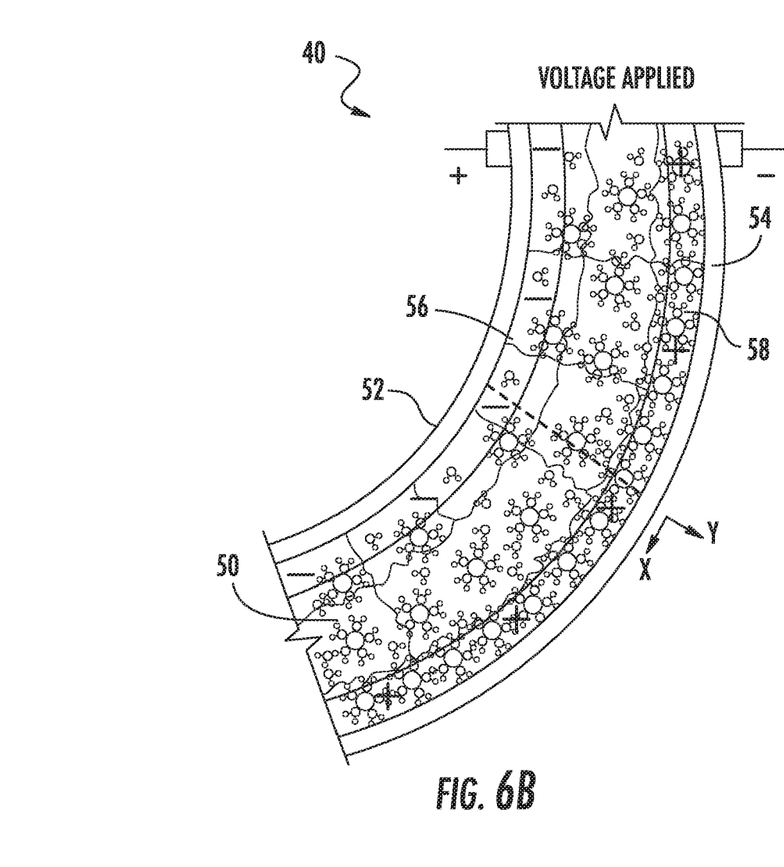
FIG. 6B is a cross-sectional view of a solid state flexible actuator in an actuated state according to an embodiment.
Figure 8:
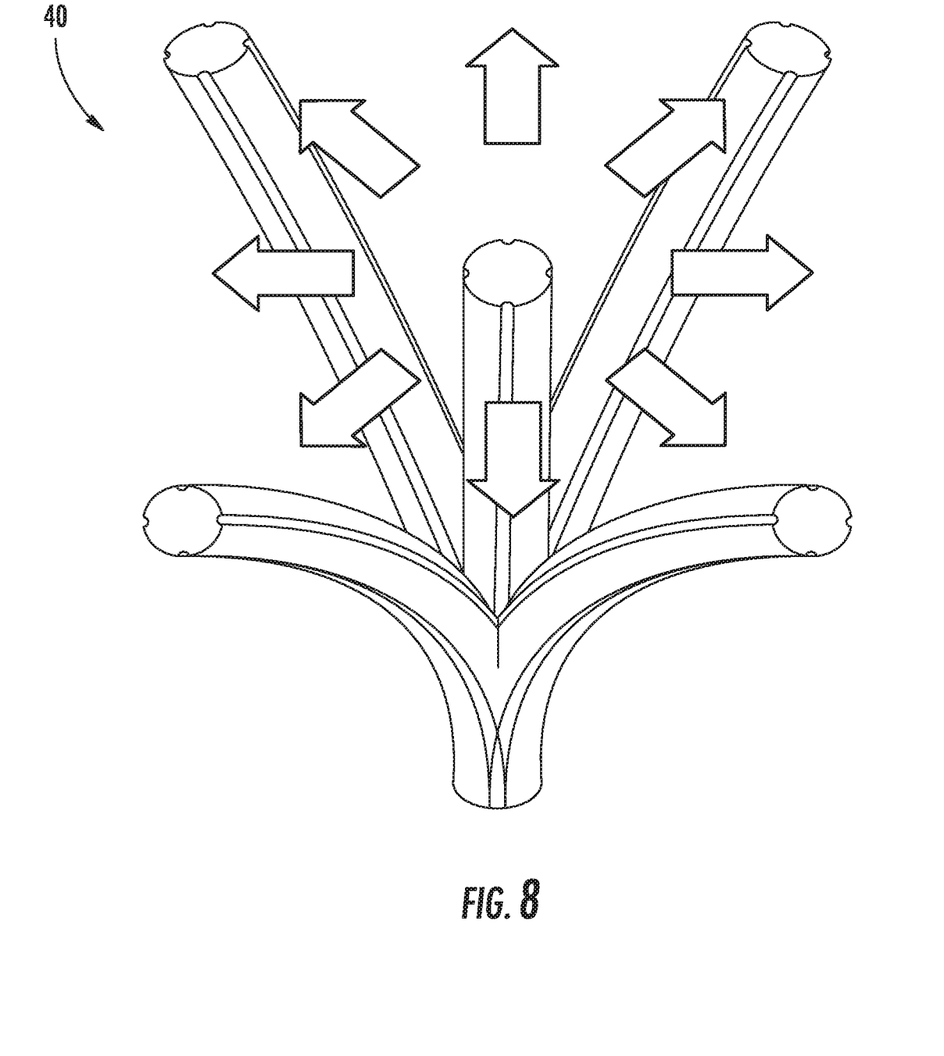
FIG. 8 is a perspective view of a solid state flexible actuator indicating the various bending movement achievable according to an embodiment.

As best illustrated in FIG. 8, the polymer 50 may deflect in response to a change in electric field provided by the electrodes 52, 54. With reference now to FIG. 6B, an example of the actuator 40 when deflected is illustrated. As shown, the electrodes 52, 54 are generally compliant and change shape with the polymer 50. Deflection of the polymer 50 in response to a change in electric field provided by the electrodes 52, 54, indicated by the negative and positive signs arranged adjacent the edges of the polymer 50 is referred to as 'actuation'. Actuation typically involves the conversion of electrical energy to mechanical energy. As the polymer 50 changes in size, the deflection may be used to produce mechanical work. As used herein, the term "deflection" may refer to any displacement, expansion, contraction, torsion, linear or area strain, or any other deformation of a portion of the polymer.

For actuation, the polymer 50 generally continues to deflect until the mechanical forces balance the electrostatic forces driving the deflection. The mechanical forces include elastic restoring forces of the polymer material 50, the compliance of electrodes 52, 54, and any external resistance provided by a device and/or load coupled to the actuator 40. The deflection of the actuator 40 as a result of an applied voltage may also depend on a number of other factors such as the polymer dielectric constant and the size of polymer 50. In an embodiment, the electroactive polymer actuator 40 is capable of deflection in any direction.

Figure 7:
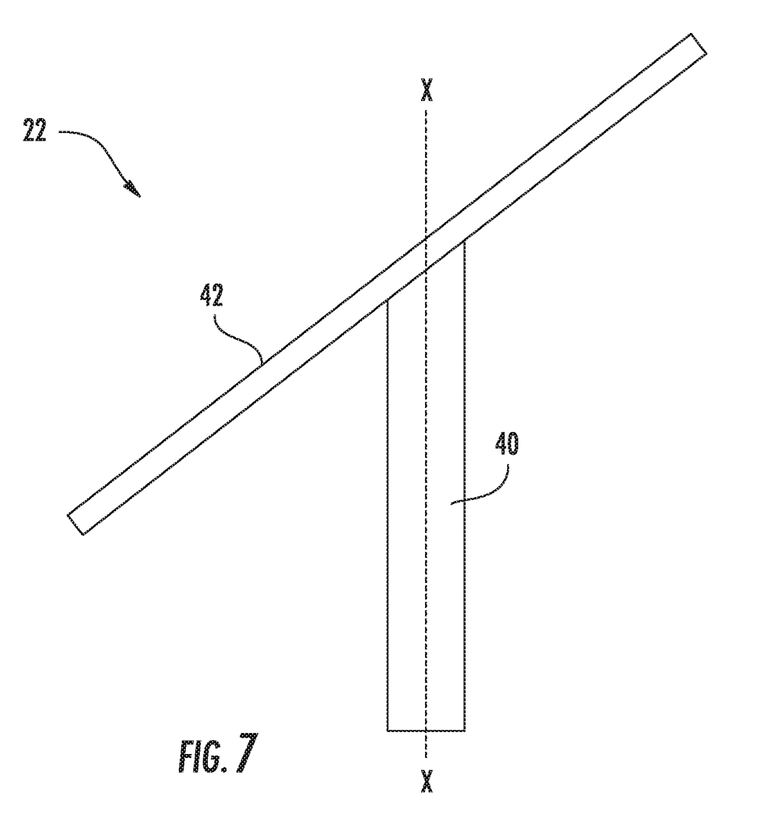
FIG. 7 is a perspective view of a mirror directly coupled to a solid state flexible actuator according to an embodiment.

In the illustrated, non-limiting embodiments, the actuator 40 is generally cylindrical in shape, generated by rolling one or more sheets of polymer 50. However, it should be understood that any suitable shape is contemplated herein. Further, the solid state flexible actuator 40 may be directly coupled to optical surface 42 or the scanner 22 as shown in FIG. 7. In such embodiments, deflection of the actuator 40 may include bending due to the displacement of the ions within the matrix of the polymer material 50. By controlling the magnitude and direction of a voltage difference between the electrodes 52, 54 of the actuator 40, the direction of bending of the actuator 40 may be manipulated to rotate the optical surface 42 or scanner 22 about an axis, such as vertical axis X for example.

Figure 9:
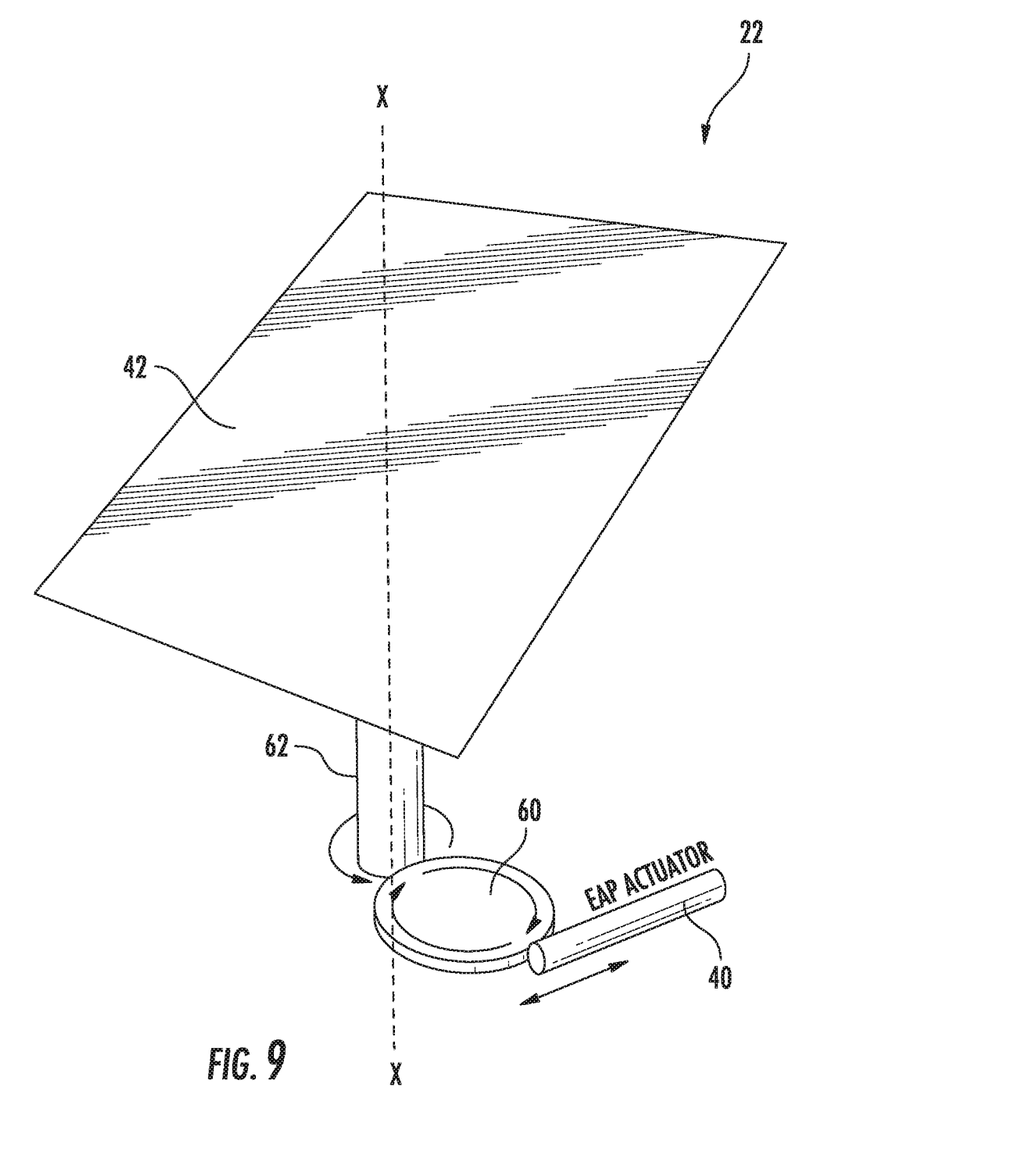
FIG. 9 is a perspective view of a mirror indirectly coupled to a solid state flexible actuator according to an embodiment.

Alternatively, the actuator 40 may be indirectly coupled to the optical surface 42 or scanner 22, as shown in FIG. 9 such as via a coupling or connector for example. In such embodiments, the actuator 40 may be constructed to achieve a linear deflection, resulting in elongation or compression of the actuator 40. In the illustrated, non-limiting embodiment, this linear movement of the actuator 40 may be used to drive rotation of a coupling 60 about an axis. The coupling 60 may be directly or indirectly engaged with a shaft 62 supporting the optical surface 42 or scanner 22 such that the rotation of the coupling 60 is transmitted to the shaft 62 to rotate the optical surface 42.

Use of a solid state flexible actuator 40 to control movement of the scanner or the optical surface 42 provides better control than existing actuators 40. Because the solid state flexible actuator 40 has a limited number of moving parts, the overall reliability of the scanner 22 is increased. Further, the actuator 40 is very light weight and small in size, requiring extremely low power for operation. As a result, the cost of such an actuator 40, as well as the cost of operating such an actuator 40, is potentially reduced compared to existing motors. In addition, a solid state flexible actuator 40 as described herein provides better control of movement relative to the scanning space, resulting in improved accuracy and response time. In embodiments where the scanner 22 is used to detect the presence of a smoke particle, a fire, or another contaminant, the actuator 40 may be operated to focus the optical surface 42 or scanner 22 at a known location, i.e. where the presence of a particle or object was detected. This direction of the optical surface 42 towards a specific location may occur without having to rotate the scanner 22 through the full range of motion and perform corresponding sampling associated with such rotation prior to reaching the desired location (each of which is likely to cause additional delay in evaluating a potentially hazardous detected condition).

Dust and debris or any particles may collect on the optical surface 42 used to direct the light into the adjacent area being monitored. The presence of such debris can change and degrade the strength of the light signal, thereby impacting the effectiveness and accurateness of the monitoring system 20. In an embodiment, the actuator 40 may be operated in such a manner to agitate or shake the optical surface 42, thereby reducing or preventing the accumulation of debris on the optical surface 42 in addition to removing debris from the optical surface 42. Such operation typically requires movement of the actuator 40 at a very high frequency, such as between 1 Hz and 1 kHz, and up to between 1 Hz and 5 kHz. For example, the actuator 40 may be manipulated to repeatedly transition movement of the actuator 40 between rotation in a first direction and rotation in a second, opposite direction.

Figure 10:
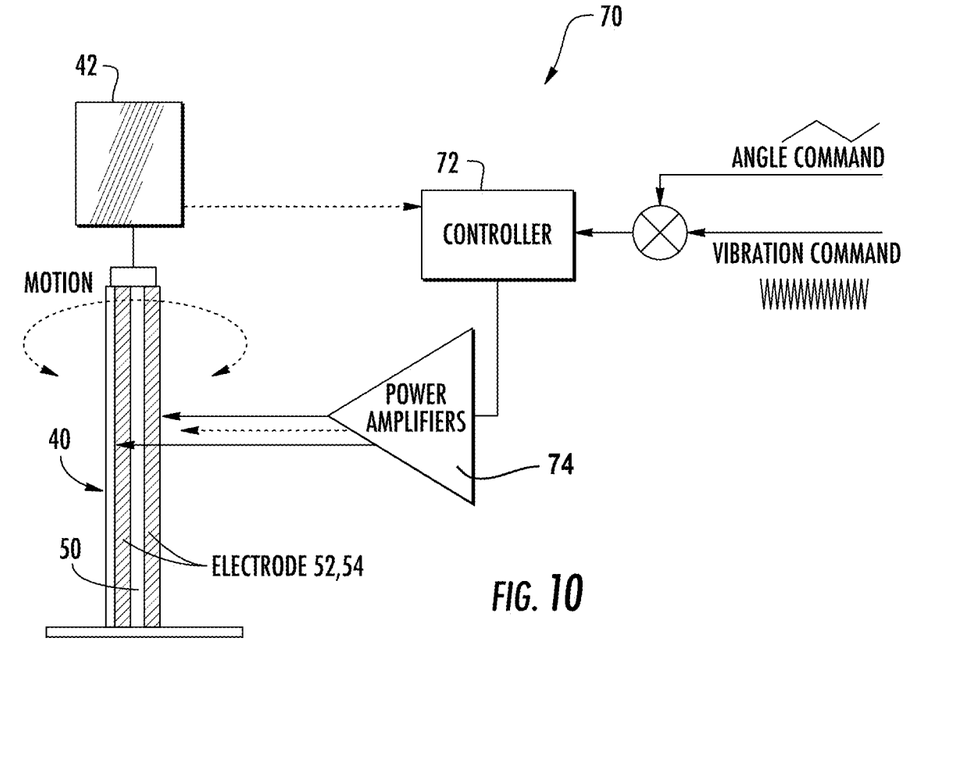
FIG. 10 is a schematic diagram of a system for controlling operation of an actuator to agitate the optical surface according to an embodiment.

With reference now to FIG. 10, an example of a control system 70 for controlling movement of the actuator to "vibrate" or clean the optical surface 42 is illustrated. As shown, the control system 70 includes a controller 72. In an embodiment, the controller 72 of the control system 70 is the same controller 31 previously described with respect to the light source 28 and light sensitive device 30 of the detector 22. In some embodiments a separate controller 72 may be used in the control system 70. In an embodiment, the controller 72 is configured to receive an angle command and a vibration command for excitation of the actuator 40. The angle command and the vibration command may be generated by a microcontroller (not shown), or alternatively, from a fire panel module (not shown) operably coupled to the controller 72. Using these commands, the controller 72 generates a signal including one or more parameters associated with the energy to be applied to the electrodes 52, 54 of the actuator 40, such as energized pulse frequency, duration, and amplitude for example, to achieve an agitating motion of the optical surface 42. In an embodiment, the signal output from the controller 72 may be communicated to an amplifier 74 prior to being supplied to the electrodes 52, 54. However, embodiments that do not include an amplifier are also contemplated herein.

Figure 11:
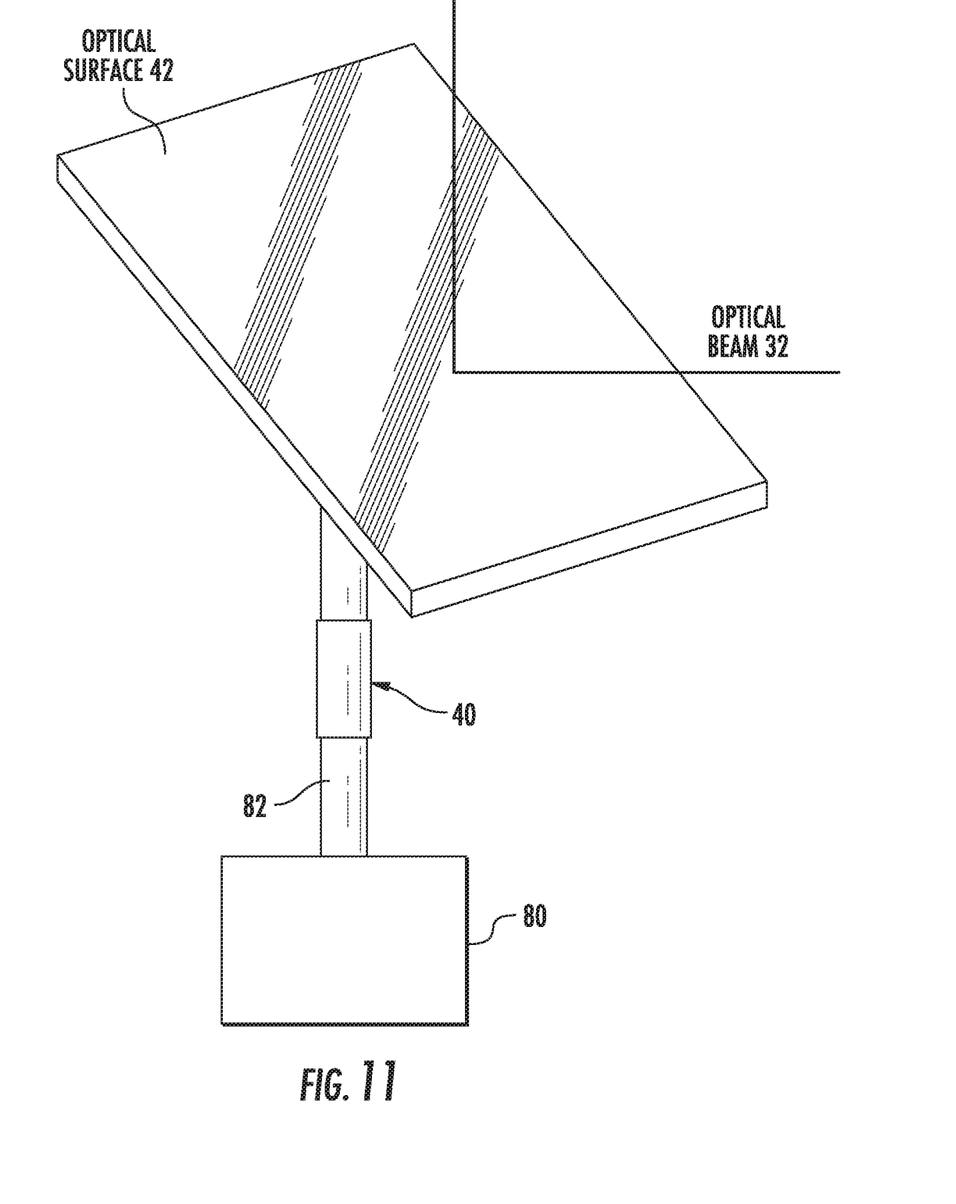
FIG. 11 is a perspective view of a scanner including an actuator attachment for indirectly coupling an electromechanical actuator to an optical surface according to an embodiment.

The electromechanical actuators that are typically used to rotate the optical surface 42 or the scanner 22 are incapable of rotating the optical surface 42 or scanner 22 with a frequency or degree of freedom sufficient to remove debris from the optical surface 42. With reference now to FIG. 11, an embodiment is illustrated that enables retrofit of an existing scanner 22 which prior to retrofit is driven by an electromechanical actuator, illustrated schematically at 80. Scanner 22 may be modified or retrofit to additionally include a solid state flexible actuator 40 to perform high-frequency cleaning operations. In the illustrated, non-limiting embodiment, the electromechanical actuator 80 includes an output shaft 82 operably coupled to a base or other portion of the optical surface 42. During normal operation, the electromechanical actuator 80 may be used to rotate the optical surface 42 or scanner 22 about an axis. A separate, solid state flexible actuator 40 may be coupled to the shaft 82. In an embodiment, the shaft 82 is formed in two portions and the actuator 40 is arranged between the two portions. Alternatively, the actuator 40 may be mounted circumferentially with the shaft 82. Regardless of how the connection is formed, the solid state flexible actuator 40, which is operable at higher frequencies than the electromechanical actuator 80, may be used to control rotation of the shaft 82 during cleaning operations. However, in other embodiments of a retrofit application, the solid state flexible actuator 40 coupled to the shaft 82 may be used in addition to, or as an alternative to the electromechanical actuator 80 to drive rotation of the optical surface 42 or scanner 22 about an axis during normal operation.

A cleaning or agitation operation as described herein may occur in response to detection of a degradation of the strength of the light pulse 32 emitted by the light source 28, such as beyond a threshold degradation of strength, or alternatively or in addition, may occur at predetermined time intervals, such as every 6 hours for example. The cleaning or agitation operation may similarly cease after a fixed period of time, such as on the order of 30 seconds or 1 minute, for examples. However, in other embodiments, the cleaning operation may continue until the strength of the light pulse 32 has increased to above a suitable level or threshold, wherein operation of the device 22 is not negatively impacted. Alternatively, or in addition, periodic agitation may occur on a schedule.

Use of a solid state flexible actuator 40 to provide an agitating movement for cleaning the optical surface 42 allows for automatic dirt removal or cleaning or the optical surface. This cleaning eliminates the needs for manual cleaning, while preventing degradation of the light pulse signal strength. In addition, because the solid state flexible actuator 40 has a limited number of moving parts, the overall reliability of the scanner 22 is increased. Further, the actuator 40 is very light weight and small in size, requiring extremely low power for operation. For example, a solid state flexible actuator 40 typically requires tens of milliWatts (mW) whereas existing electromechanical actuators require hundreds of mW or more. As a result, the cost of such an actuator 40, as well as the cost of operating such an actuator 40, is potentially reduced compared to existing motors.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A scanner of an optical detection system comprising:
   a housing;
   an optical surface coupled to the housing, the optical surface being movable to direct light into an area being scanned and to receive a reflected light pulse from the area being scanned;
   an electromechanical actuator having an output shaft operably coupled to the optical surface, wherein the electromechanical actuator is operable to rotate the optical surface during normal operation; and
   a solid state flexible actuator, separate from the electromechanical actuator, the solid state flexible actuator being operably coupled to the output shaft, wherein the solid state flexible actuator is operable to rotate the optical surface during a cleaning operation, the solid state flexible actuator being operable at a higher frequency than the electrometrical actuator.

2. The scanner of claim 1, further comprising:
   a light source associated with the housing operable to emit a light pulse into the area being scanned; and
   a light sensitive device associated with the housing operable to detect the reflected light pulse from the area being scanned.

3. The scanner of claim 1, wherein the solid state flexible actuator agitates the optical surface at a frequency between about 1 Hz and 1 kHz.

4. The scanner of claim 1, wherein the solid state flexible actuator is selectively operable to rotate the optical surface about at least one axis relative to the housing.

5. The scanner of claim 1, wherein the solid state flexible actuator comprises a solid state flexible polymer deformable in response to application of a voltage to the solid state flexible polymer.

6. The scanner of claim 5, wherein the solid state flexible actuator is directly coupled to the optical surface.

7. The scanner of claim 5, wherein the solid state flexible actuator is indirectly coupled to the optical surface.

8. The scanner of claim 5, wherein the solid state flexible actuator further comprises a first electrode and a second electrode operable to apply the voltage to the solid state flexible polymer.

9. The scanner of claim 5, wherein the solid state flexible polymer comprises an electroactive polymer.

10. The scanner of claim 5, wherein the solid state flexible polymer comprises a piezoelectric material.

11. The scanner of claim 5, wherein the solid state flexible polymer comprises a dielectric polymer.

12. A smoke detection system comprising:
    at least one scanner of claim 1; and
    a central processing unit in communication with the at least one scanner.

13. A method of cleaning a scanner of a detection system comprising:
    agitating an optical surface of the scanner via an electromechanical actuator at a first frequency, the electromechanical actuator having an output shaft operably coupled to the optical surface;
    initiating a cleaning operation; and
    rotating the optical surface of the scanner via a solid state flexible actuator, the solid state flexible actuator being separate from the electromechanical actuator, wherein the optical surface is rotated by the solid state flexible actuator at a second frequency, the second frequency is greater than the first frequency and is at least 1 Hz.

14. The method of claim 13, wherein the frequency is between 1 Hz and 1 kHz.

15. The method of claim 13, wherein initiating the cleaning operation occurs in response to detection of a degradation of strength of a light pulse emitted from the scanner.

16. The method of claim 13, wherein initiating the cleaning operation occurs at designated time intervals.

17. The method of claim 13, wherein rotating the optical surface of the scanner at a frequency of at least 1 Hz via the solid state flexible continues for a predetermined period of time.

18. The method of claim 13, wherein rotating the optical surface of the scanner at a frequency of at least 1 Hz via the solid state flexible continues until a strength of a light pulse emitted from the scanner has increased beyond a threshold.

19. The method of claim 13, wherein rotating the optical surface of the scanner at a frequency of at least 1 Hz via the solid state flexible actuator occurs in response to a command from a controller.

* * * * *